United States Patent
Lecursi et al.

(10) Patent No.: US 11,911,306 B2
(45) Date of Patent: Feb. 27, 2024

(54) DOUBLE ACTING ORTHOTIC JOINT, ORTHOSIS AND METHODS OF USE

(71) Applicant: Becker Orthopedic Appliance Company, Troy, MI (US)

(72) Inventors: Nicholas Lecursi, Saline, MI (US); Beatrice Janka, Rochester Hills, MI (US)

(73) Assignee: Becker Orthopedic Appliance Company, Troy, MI (US)

( * ) Notice: Subject to any disclaimer, the term of this patent is extended or adjusted under 35 U.S.C. 154(b) by 0 days.

(21) Appl. No.: 17/784,534

(22) PCT Filed: Dec. 10, 2020

(86) PCT No.: PCT/US2020/064287
§ 371 (c)(1),
(2) Date: Jun. 10, 2022

(87) PCT Pub. No.: WO2021/119294
PCT Pub. Date: Jun. 17, 2021

(65) Prior Publication Data
US 2023/0018788 A1   Jan. 19, 2023

Related U.S. Application Data

(60) Provisional application No. 62/946,338, filed on Dec. 10, 2019.

(51) Int. Cl.
*A61F 5/01* (2006.01)
(52) U.S. Cl.
CPC .......... *A61F 5/0102* (2013.01); *A61F 5/0127* (2013.01); *A61F 2005/0167* (2013.01); *A61F 2005/0179* (2013.01)

(58) Field of Classification Search
CPC ...... A61F 2005/0165; A61F 2005/0167; A61F 2005/0169; A61F 2005/0179; A61F 2005/0197; A61F 5/0102; A61F 5/0127
See application file for complete search history.

(56) References Cited

U.S. PATENT DOCUMENTS

| 5,328,444 | A | 7/1994 | Whiteside |
| 6,001,075 | A | 12/1999 | Clemens et al. |

(Continued)

FOREIGN PATENT DOCUMENTS

| EP | 2506811 B1 | 3/2017 |
| WO | WO2009015473 | 2/2009 |

OTHER PUBLICATIONS

ISA/US International Search Report, PCT International Application No. PCT/US2020/64287, International Filing Date Dec. 10, 2020, Applicant Becker Orthopedic Appliance Company, ISA/US dated Mar. 10, 2021, 2 pages.

(Continued)

*Primary Examiner* — Keri J Nelson
(74) *Attorney, Agent, or Firm* — Hinshaw & Culbertson LLP; Roger M. Masson, Esq.

(57) ABSTRACT

An orthotic joint device has an attachment member rotatably attached to the joint device for rotation in a first direction, a resistive element such as a spring, and a first lever for transmitting a first direction resistance force from the resistive element to the attachment member. The resistive element may also resist rotation in the second direction opposed to the first via a second lever. The orthotic joint device may be used in an orthosis and in a method of supporting an ankle of a human.

20 Claims, 10 Drawing Sheets

(56) References Cited

U.S. PATENT DOCUMENTS

2014/0142483 A1   5/2014   Jackson, Jr.
2014/0276304 A1   9/2014   Dollar et al.
2017/0231854 A1   8/2017   Herr et al.

OTHER PUBLICATIONS

European Patent Office (EPO) Supplementary European Search Report dated Nov. 17, 2023; EP Application No. 20898575.4.
European Patent Office (EPO) Extended European Search Report Communication with European Search Opinion; EP Application No. 20898575.4 dated Dec. 14, 2023.

DOUBLE ACTING ORTHOTIC JOINT, ORTHOSIS AND METHODS OF USE

CROSS-REFERENCE TO RELATED APPLICATIONS

This application is a national stage entry of International Application No. PCT/US2020/064287, filed Dec. 10, 2020 which claims priority to U.S. Application No. 62/946,338, filed Dec. 10, 2019, the contents of which are incorporated herein by reference in their entirety.

FIELD OF THE INVENTION

The present invention relates to joints for orthoses and orthoses employing those joints, typically ones that assist a wearer's ankle joint during walking, such as ankle-foot orthoses (AFO) and knee-ankle-foot orthoses (KAFO). More particularly, it relates to devices that assist the wearer's ankle joint by resisting dorsiflexion and plantarflexion of the user's ankle.

BACKGROUND

As the population ages and pathologies affecting the aging population become more prevalent, assistive devices such as orthoses are becoming increasingly common. The provision of orthotic medical procedures for these patients is complicated but provides a variety of benefits for treating and rehabilitating aging patients, particularly ones having suffered from neurological pathologic conditions such as stroke. Recent advances in orthotic components have demonstrated that increased resistive torque is required for these orthotic devices. The torque required to treat these pathologies is high and joints that can deliver that torque are becoming increasingly larger to accommodate bigger springs and other resistive elements. Bigger orthotic joints have the disadvantages of higher weight attached to the leg, poor cosmesis with lower patient acceptance and bulkier orthotic designs.

AFO and KAFO orthoses improve patient gait function by controlling stance and swing phase gait kinematics. Evidence and clinical orthotic practice suggest that these devices should be customized and fine-tuned for best results and greatest impact on patient function. This tuning of the orthotic component's resistance, alignment and range of motion settings is typically done using observational gait analysis with or without instrumentation to help identify specific swing and stance phase gait abnormalities. For many patients whose condition and supportive needs vary through their recovery from stroke or other pathologic neuromotor conditions, this tuning may need to be repeated and the component readjusted. This readjustment often means that orthotic parts may need to be swapped out to achieve the desired mechanical characteristics of the orthosis. This means that orthotists, distributors and manufacturers should maintain an inventory of parts which may increase cost of care, not only through parts costs, but through the time necessary to interchange components for the purpose of reconfiguring the component to accommodate the patient's condition. This can also increase the time of the patient's visit, and sometimes delay treatment if parts are lost or are unavailable.

In view of the above, a need exists for a compact orthotic joint providing a high torque in a small form factor and having a high degree of adjustability without having to swap out parts.

SUMMARY OF THE INVENTION

In a first embodiment of the invention, an orthotic joint device is provided. The device has an attachment member rotatably attached to the joint device for rotation in a first direction and in a second direction opposed to the first direction. The device also has a resistive element for resisting rotation of the attachment member in the first direction and a first lever for transmitting a first direction resistance force from the resistive element to the attachment member. The resistive element resists the rotation of the attachment member in the first direction when the attachment member's rotation in the first direction exceeds a first direction rotation threshold. The attachment member may be a bar or a rail box for accepting a bar. The first direction rotation threshold may be zero relative to a neutral axis. Preferably, the device has a joint body which has a pivot around which the attachment member rotates. The first lever may be separate from the attachment member or may be part of the attachment member.

The device may also have a first pivot for the first lever and a first mechanical advantage of the resistive element acting on the attachment member by the first lever. The location of the first pivot is selectable to select the first mechanical advantage. Preferably, the device has a plurality of first lever apertures and a first lever pivot pin such that the location of the first pivot is selectable by placing the first lever pivot pin in one of the first lever apertures. Preferably, the plurality of first lever apertures has an aperture in which placement of the first lever pivot pin prevents rotation of the attachment member in the first direction. In some circumstances, it is desirable for the first lever to have the first lever apertures. It is also possible, for the first lever apertures to not be in the first lever, but instead be in the joint body and thereby act as fulcrums.

The device may also have a first link such that the first lever presses against the first link and the first link presses against the resistive element when rotation of the attachment member in the first direction exceeds the first direction rotation threshold. The first link typically converts the rotation of the lever into a translation motion. The pressing may be direct or indirect, but direct is preferred. Indirect pressing may occur because another link is used to transmit the pressing. If the resistive element is a leaf spring, a cantilever spring or a flexure element integral to the joint body it may be possible to omit the first link with little detriment. Preferably, the first link has a first follower having a first follower shoulder and the device has a first follower seat such that the first follower shoulder is engaged with the first follower seat when rotation of the attachment member in the first direction is less than the first direction rotation threshold and is not engaged with the first follower seat when the rotation of the attachment member in the first direction exceeds the first direction rotation threshold. Preferably, the first follower has a first follower surface against which the first lever presses when the attachment member's rotation in the first direction exceeds the first direction threshold. The first lever has a neutral angle position when the attachment member is in a neutral position and the first lever is in contact with the attachment member such that the first direction threshold is a function of a distance between the first follower surface and the first lever in the neutral angle position. This distance can be adjustable or fixed. Preferably, the device has a neutral angle, which is the central axis for at least an upper portion of the attachment member when the attachment member is in a position at which the spring element does not exert a net force on the attachment member and the first follower has a direction of travel that is substantially perpendicular to the direction of travel.

Preferably, the resistive element has a spring element and the device has a neutral axis that is the central axis for at least an upper portion of the attachment member when the attachment member is at rest and in a position at which the spring element does not exert a net force on the attachment member. Preferably, the spring element has a coil spring, machined helical spring or cup springs having an axis of compression that is substantially perpendicular to the neutral angle. Substantially perpendicular is defined as being within 15° or π/12 radians of perpendicular. More preferably, the axis of compression is within 10° (π/18 radians) and most preferably, within 5° (π/36 radians) of being perpendicular to the axis of compression. Should the axis of compression not be in the same plane as the neutral angle, whether or not there is substantial perpendicularity/the angle between the axis of compression and the neutral angle should be determined by projecting the axis of compression onto a plane that is parallel to the axis of compression and containing the neutral angle and then by measuring the angle of the projected axis of compression to the neutral angle.

The resistive element may have a spring element, which may be a coil spring, a coil spring co-molded within a polymer matrix, a machined helical spring, a polyurethane spring, a gas spring, cup springs, a damper, a torsion spring, a leaf spring, a cantilever spring, a flexure element that is integral to a joint body of the device, and combinations of springs from this list. The cantilever spring could have a v shape, u shape, horseshoe shape or serpentine shape as best suits the rate and desired deflection of the spring as well as the desired shape as relates to the component body. The resistive element may have any of the springs listed for the spring element in this paragraph, a damper or a dashpot.

The device can have a first adjustable range of motion limiter for limiting the range of motion in the first direction. Preferably, the device has a first threaded passage, typically in the joint body, and the first adjustable range of motion limiter has a first threaded screw whose location in the first passage is adjustable by screwing the first threaded screw in or out. Preferably, the first adjustable range of motion limiter limits the rotation in the first direction by contact with the first lever.

The device can have a first adjustable preload spring for adjusting the preload force resisting the rotation of the attachment member in the first direction.

The resistive element can also have a stop, a motion limiter, or a sensor for sensing the force resisting the rotation of the attachment member in the first direction.

The above-described joint can be used to provide resistance in one direction to a user of the joint device, but preferably also provides resistance in both the first and second directions. In a push-push embodiment, the joint provides resistance in both directions. Two different resistive elements may be used in this configuration, but for increased compactness the same resistive element can be used for resistance in both the first and second directions. Accordingly, the single resistive element push-push embodiment has a second lever that is similar to the first lever, but is for transmitting a second direction resistance force from the resistive element to the attachment member such that the resistive element also resists the rotation of the attachment member in the second direction when the attachment member's second direction rotation exceeds a second direction rotation threshold. This embodiment can also have an adjustable second pivot, second lever apertures, a second lever pivot pin, a second link, a second follower, a second follower seat, a second adjustable range of motion limiter, and a second adjustable preload spring that are similar or identical to the adjustable first pivot, the first lever apertures, the first lever pivot pin, the first link, the first follower, the first follower seat, the first adjustable range of motion limiter, and the first adjustable preload spring except that the second ones of these, e.g., second lever, second link and second adjustable preload spring, are for resisting movement in the second direction.

Preferably, the resistive element has a spring element and the device has a first follower such that the first lever presses against the first follower and the first follower presses against the spring element when rotation of the attachment member in the first direction exceeds the first direction rotation threshold. Also the device has a second follower such that the second lever presses against the second follower and the second follower presses against the spring element when rotation of the attachment member in the second direction exceeds the second direction rotation threshold. Preferably, the first follower has a first follower shoulder and the device also has a first follower seat. When rotation of the attachment member is less than the first direction rotation threshold, the first follower shoulder is engaged with the first follower seat and is not engaged with the first follower seat when rotation of the attachment member in the first direction exceeds the first direction rotation threshold. Preferably, the second follower has a second follower shoulder and the device also has a second follower seat. When rotation of the attachment member in the second direction is less than the second direction rotation threshold, the second follower shoulder is engaged with the second follower seat and is not engaged with the second follower seat when rotation of the attachment member in the second direction exceeds the second direction rotation threshold. Preferably, the spring element is located between the first and second follower seats. Preferably, the spring element presses the second follower shoulder against the second follower seat to generate the first direction resistance force and the spring element presses the first follower shoulder against the first follower seat to generate the second direction resistance force. Preferably, the device also has a follower distance between the first and second followers when the first and second follower shoulders are engaged with first and second follower seats, respectively. The attachment member has a first range of rotation which is a function of the follower distance.

In one embodiment, the joint has a push-pull configuration in which first lever is connected to the resistive element by a link and the first lever is connected to the attachment member by another link.

In a second embodiment of the invention, an ankle foot orthosis for a human is provided. The orthosis has an orthotic joint device as described above in which the attachment member constitutes a first attachment member. The orthosis has a second attachment member attached to the orthotic joint device. One of the first attachment member and the second attachment member is configured for attachment to a lower leg of the human, and the other being configured for attachment to a foot of the human. Preferably, the first direction is a plantarflexion direction and the second direction is a dorsiflexion direction. Preferably, the orthosis has a joint body and the second attachment member is configured for attachment to the lower leg and can be rotated and locked relative to the joint body.

In a third embodiment of the invention, a method of supporting an ankle of a human in a range of dorsiflexion and plantarflexion motions is provided. The method uses the orthosis previously described. The method includes attaching the first attachment member to a lower leg or foot corresponding to said ankle and attaching the second attachment member to the other of the foot and the lower leg.

Many of the benefits of the invention relate to the first lever (and the second lever if present). By having a first lever, it is possible to position and orient the resistive element, particularly one for providing a high torque, to make the joint device more compact. Further compactness is achieved by having the resistive element, particularly a spring element, resist motion in both directions. By making the mechanical advantage of the levers adjustable, it is possible to have a high degree of adjustability without having to swap out parts.

DETAILED DESCRIPTION OF THE INVENTION

Ankle Joint

A first embodiment of a joint device 10 is discussed with reference to FIGS. 1-6. Joint device 10 has a body 12 having a pivot 14 provided by a pivot bushing 15, an attachment member 16, a resistive element for resisting rotation 18, a first lever 20a, and a second lever 20b. Body 12 may be unitary as shown or may be composed of a plurality of body parts. As illustrated, pivot 14 fits within a pivot aperture 24 in joint body 12 and is held there by any suitable means. Pivot 14 could be supported by a journal bearing, a roller bearing, or a ball bearing. Attachment member 16 pivots around pivot 14 in first and second directions 62a and 62b. As shown, attachment member 16 is a stirrup 26 and joint device 10 is an ankle joint for use in an ankle-foot orthosis or a knee-ankle-foot orthosis. Stirrup 26 may be attached to a footplate (not shown) by any suitable means. Alternatively, attachment member 16 could be a bar or rail box which in turn is attached to a stirrup. Stirrup 26 is in contact with first and second levers 20a and 20b at curved protuberances 28a and 28b at their bottom ends, respectively. As shown, first lever 20a is on the right and second lever 20b is on the left. Their relative locations could be reversed. As a matter of convention, reference letter "a" is used herein to refer to a first or one or more similar parts and "b" will be used to refer to the second one of the similar parts. Levers 20 are held in place against stirrup 26 by resistive element 18, which is illustrated as a helical compression spring 30, but could be any suitable spring such as a machined spring or a combination of springs typically having very different characteristics.

Spring 30 holds first and second links, referred herein as first and second followers 32a and 32b, which push against first and second levers 20a and 20b at curved protuberances 34a and 34b at their top ends, respectively. Each follower 32 has a cylindrical inner portion 36, a cylindrical outer portion 37, a collar 39 having an inside face 38 and an outside face 40, and end surfaces 41. Followers 32a and 32b may be identical as shown or may be different. Both inner portions 36 extend into spring 30. Spring 30 pushes against inside faces 38 pushing followers 32 outwardly. End surfaces 41 (a.k.a. follower surfaces 41) may be flat or curved. Some convexity to end surfaces 41 may be advantageous, but end surfaces 41 are shown as being flat in some figures for ease of illustration. It is possible for the cylindrical inner portions 36 to also push on an inner spring located inside spring 30 to provide supplement resistance the resistance provided by spring 30.

Followers 32 and spring 30 are located within a channel 42 in body 12. Channel 42 provides follower seats 44 for followers 32. Followers 32 (particularly outside faces 40) are seated on seats 44 as shown in FIGS. 1-6 by spring 30. Outer portions 37 extend beyond seats 44.

Returning back to levers 20, levers 20 rotate around pivots 46. Pivots 46 are shown here as pins 48. The location of pivots 46 are adjustable. This adjustability is provided by a row of pivot apertures 52 for each lever 20. Each row is parallel to its lever 20 in its neutral position, which corresponds to attachment member 16 being at the neutral angle (discussed later). As shown, pivot apertures 52 are advantageously within the levers 20 in which case two pins 48 can be inserted into a lever 20 to prevent it from rotating. Pivot apertures 52 may be located outside its corresponding lever 20 in joint body 12, but adjacent the corresponding lever in its neutral position. Joint body 12 may also have apertures 54 in alignment with pivot apertures 52 when the corresponding lever 20 is in its neutral position. Generally any apertures 52 or 54 in joint body 12 extend through joint body 12 to facilitate the removal, i.e., pushing out of pins 48.

Joint device 10 also has a range of motion limiters 56a and 56b for limiting the range of motion in the first direction and in the second direction, respectively. Limiters 56 may have a rubber bumper for contact with levers 20. Because the figures are schematic, the appearance and location of limiters 56 may vary from figure to figure. Range of motion limiters 56 have threads for threadingly engaging threads of passages 58 (in joint body 12) in which limiters 56 are installed. Limiters 56 may be screwed in or out to adjust the range of motion of attachment member 16.

Joint device 10 has an aperture 60 in joint body 12 for attachment to a second attachment member. Aperture 60 may be used for pivotally (or non-pivotally) attaching the second attachment member as disclosed in Applicant's U.S. patent application Ser. No. 14/738,212.

Operation of joint device 10 will now be discussed. FIGS. 1-6 illustrate joint device 10 with attachment member 16 at a neutral position. At the neutral position, there is no net force on attachment member 16 in the first and second directions. The neutral position typically corresponds to an upright position for a patient who is capable of standing upright. For such a patient, the axis of travel of followers 32 is horizontal.

There may be a range of free motion around the neutral axis (not shown) if first lever 20a does not contact stirrup 26 or first follower 32a or if second lever 20b does not contact stirrup 26 or second follower 32b. Preferably, as shown, first lever 20a does contact both stirrup 26 and first follower 32a, which is seated against first follower seat 44a and second lever 20b contacts both stirrup 26 and second follower 32b, which is seated against second follower seat 44b.

Figure 9:
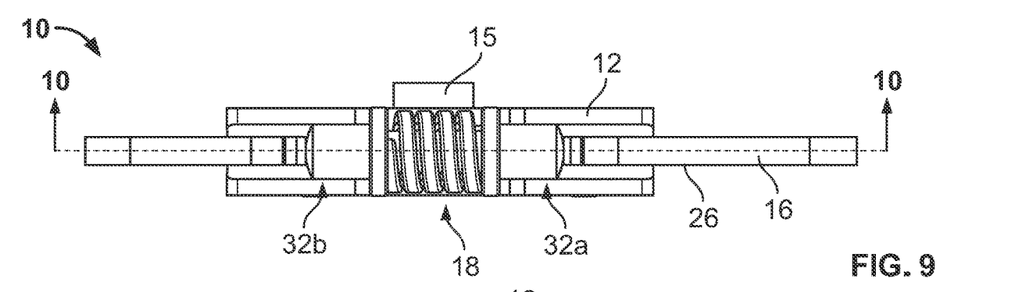
FIG. 9 is a plan view of the joint body of FIG. 1, but in plantarflexion.
Figure 10:
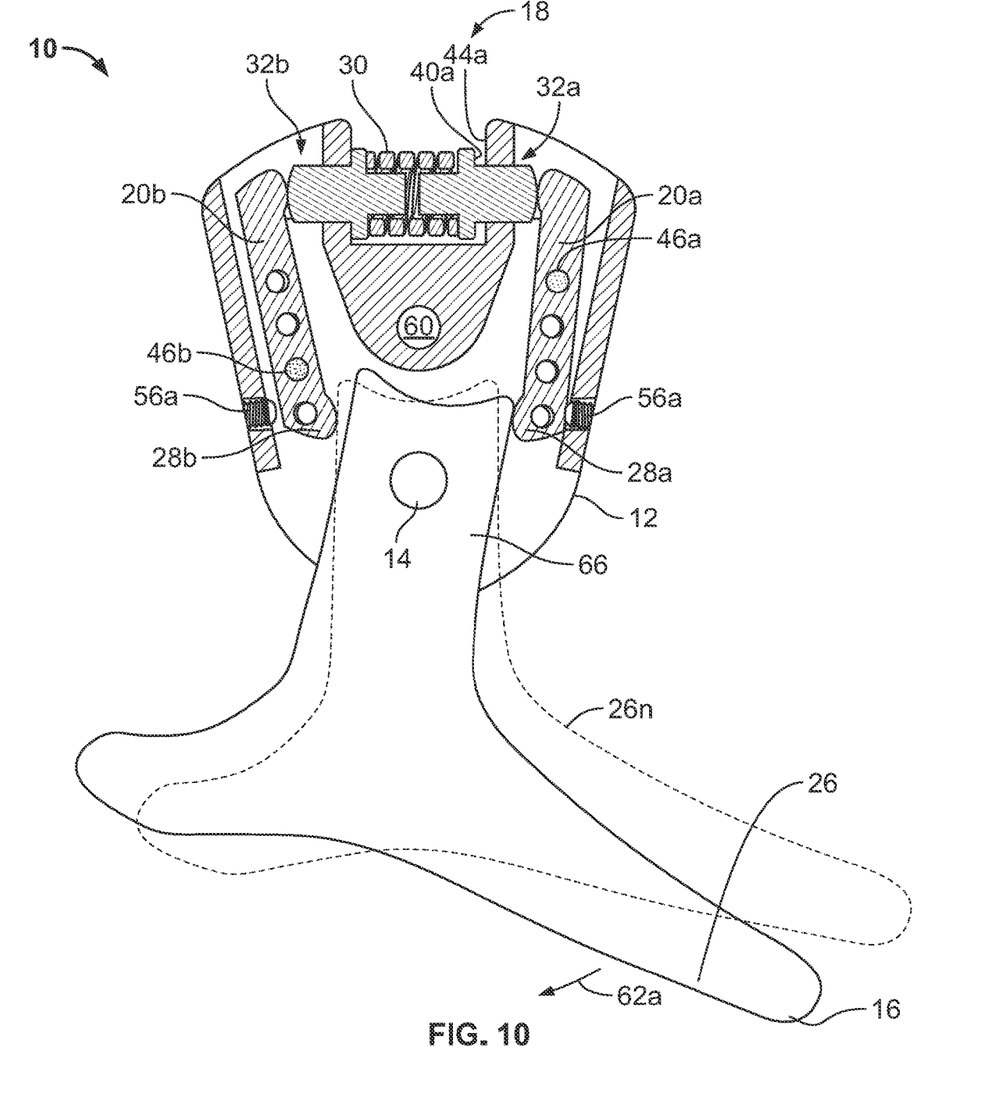
FIG. 10 is a cross-sectional view taken along line 10-10 shown in FIG. 9.
Figure 11:
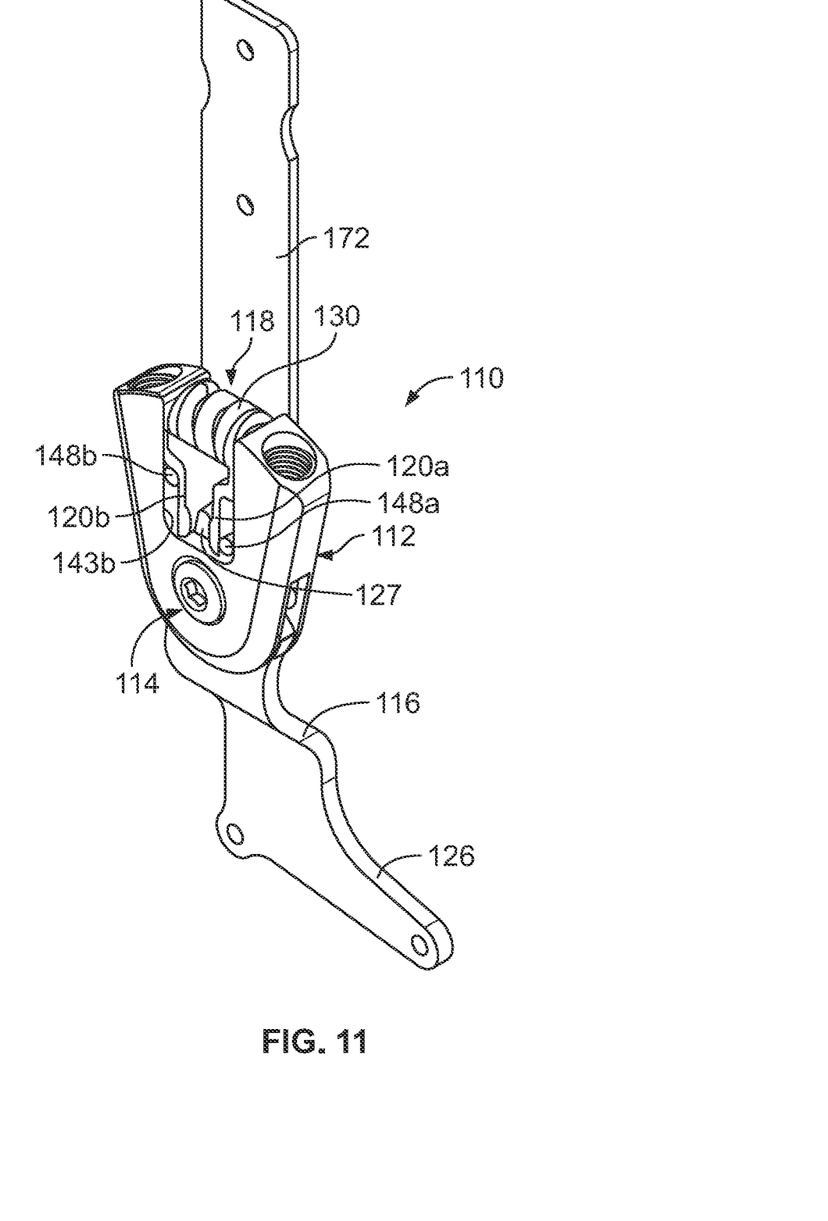
FIG. 11 is a perspective view of a second joint body for an ankle foot orthosis.
Figure 12:
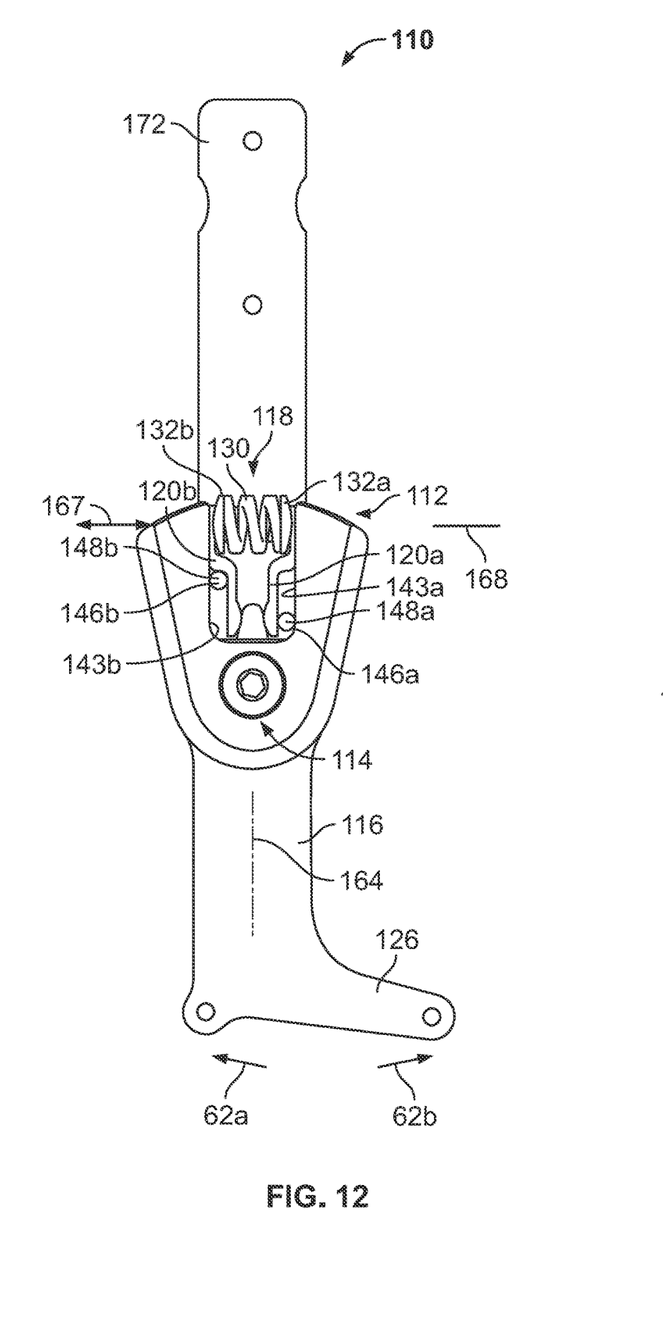
FIG. 12 is an elevation view of the joint body of FIG. 11 from one side.
Figure 13:
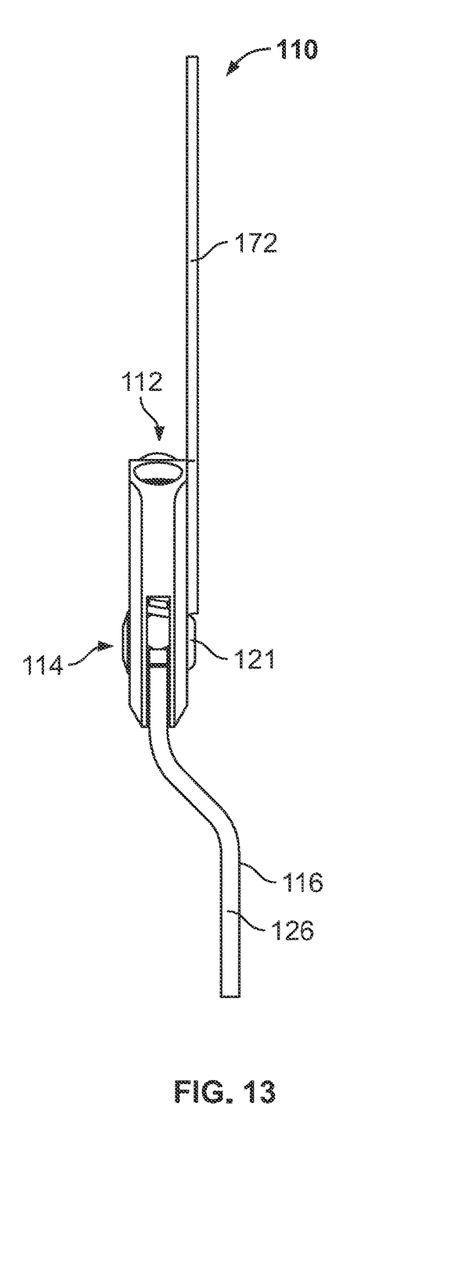
FIG. 13 is a front elevation view of the joint body of FIG. 11.

Referring now to FIGS. 9 and 10, stirrup 26 has rotated in first direction 62a (shown here as a plantarflexion direction) relative to the neutral position 26n (outline of stirrup 26 in neutral position shown in dashed lines) pushing lever 20a counterclockwise around pivot 46a until lever 20a contacted range of motion limiter 56a. Lever 20a has pushed first follower 32a to the left disengaging outside face 40a from first follower seat 44a and compressing spring 30. Stirrup 26 has rotated away from second lever 20b, which as shown remains in contact with second follower 32b which remains seated. Conceivably, second lever 20b could have rotated by gravity around pivot 46b towards stirrup 26 but away from second follower 32b as lever 20b is no longer held in place by follower 32b and stirrup 26.

Figure 7:
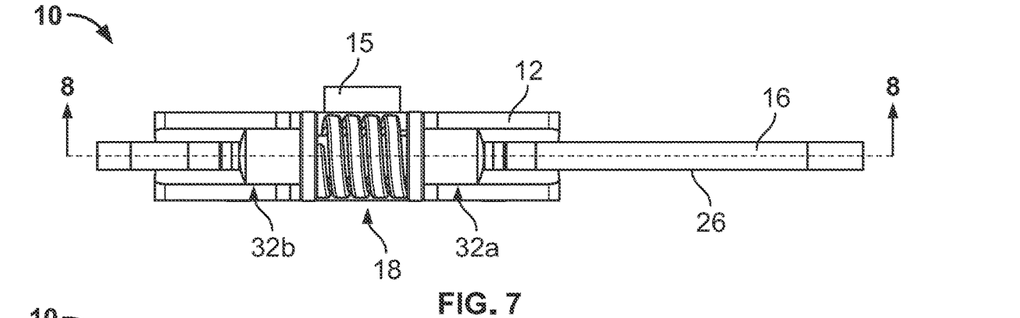
FIG. 7 is a plan view of the joint body of FIG. 1, but in dorsiflexion.
Figures 8, 8A:
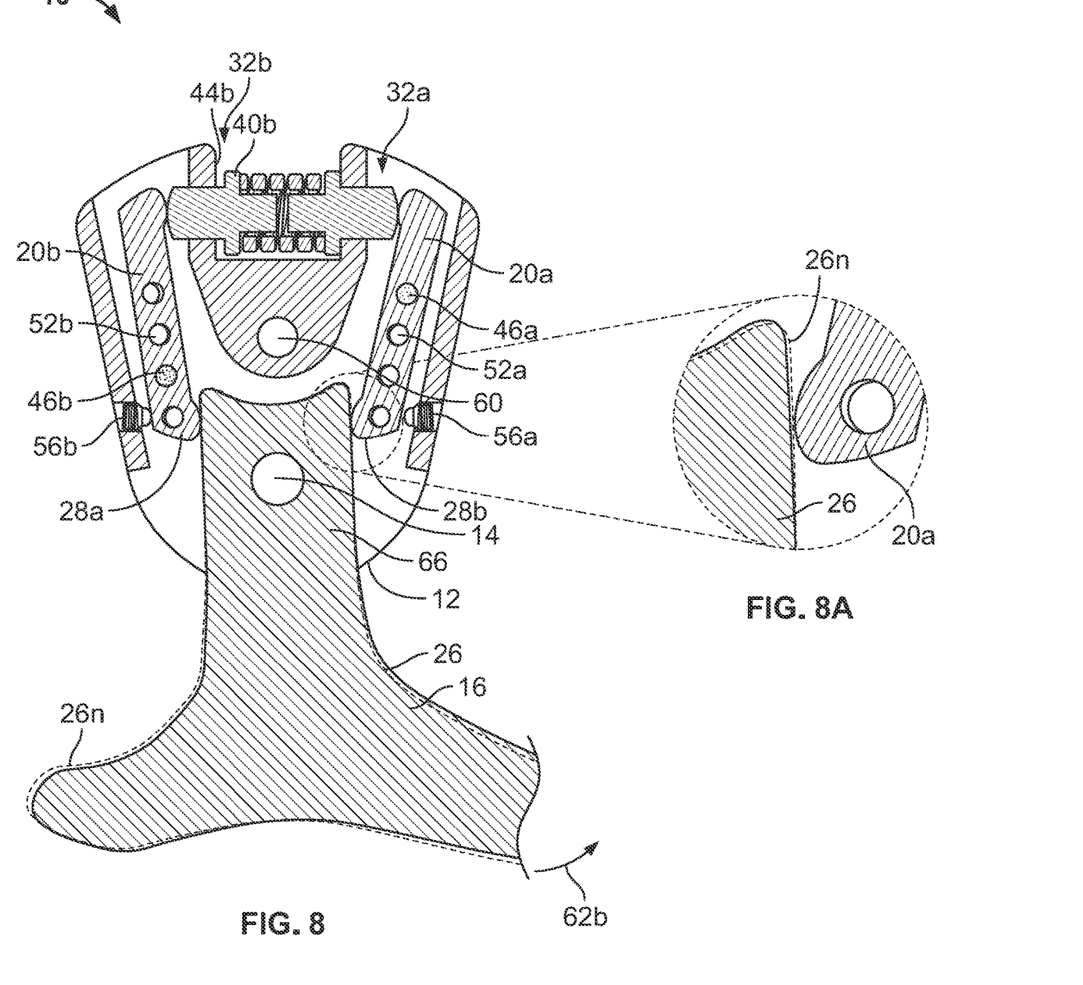
FIG. 8 is a cross-sectional view taken along line 8-8 shown in FIG. 7.
FIG. 8A is a magnified view of a circled portion of FIG. 8.

Referring now to FIGS. 7-8A, stirrup 26 has rotated in second direction 62b (shown here as a dorsiflexion direction) relative to the neutral position 26n (outline of stirrup 26 in neutral position in dashed line) pushing lever 20b clockwise around pivot 46b until lever 20b contacted range of motion limiter 56b. Lever 20b has pushed first follower 32b to the right disengaging outside face 40b from second follower seat 44b and compressing spring 30. Stirrup 26 has rotated away from first lever 20a, as best seen in FIG. 8A, which as shown remains in contact with first follower 32a which remains seated.

As can be seen from FIGS. 7-10, the location of pivots 46a and 46b determine the mechanical advantage of the resistive element 30 acting on the stirrup 26, thus determining the resistance of the stirrup 26 to rotation in the clockwise and counterclockwise directions. The travel of spring 30 in FIGS. 8 and 10 is approximately the same, but the amount of rotation of the stirrup 26 in first direction 62a in FIG. 10 is much higher than the rotation in second direction 62b in FIG. 8. In addition to affecting the amount of travel of stirrup 26, changing the location of pivot 46 affects the mechanical advantage between springs 30 and stirrup 26 and therefore the resistance of the stirrup 26 to motion at the ankle.

Figure 1:
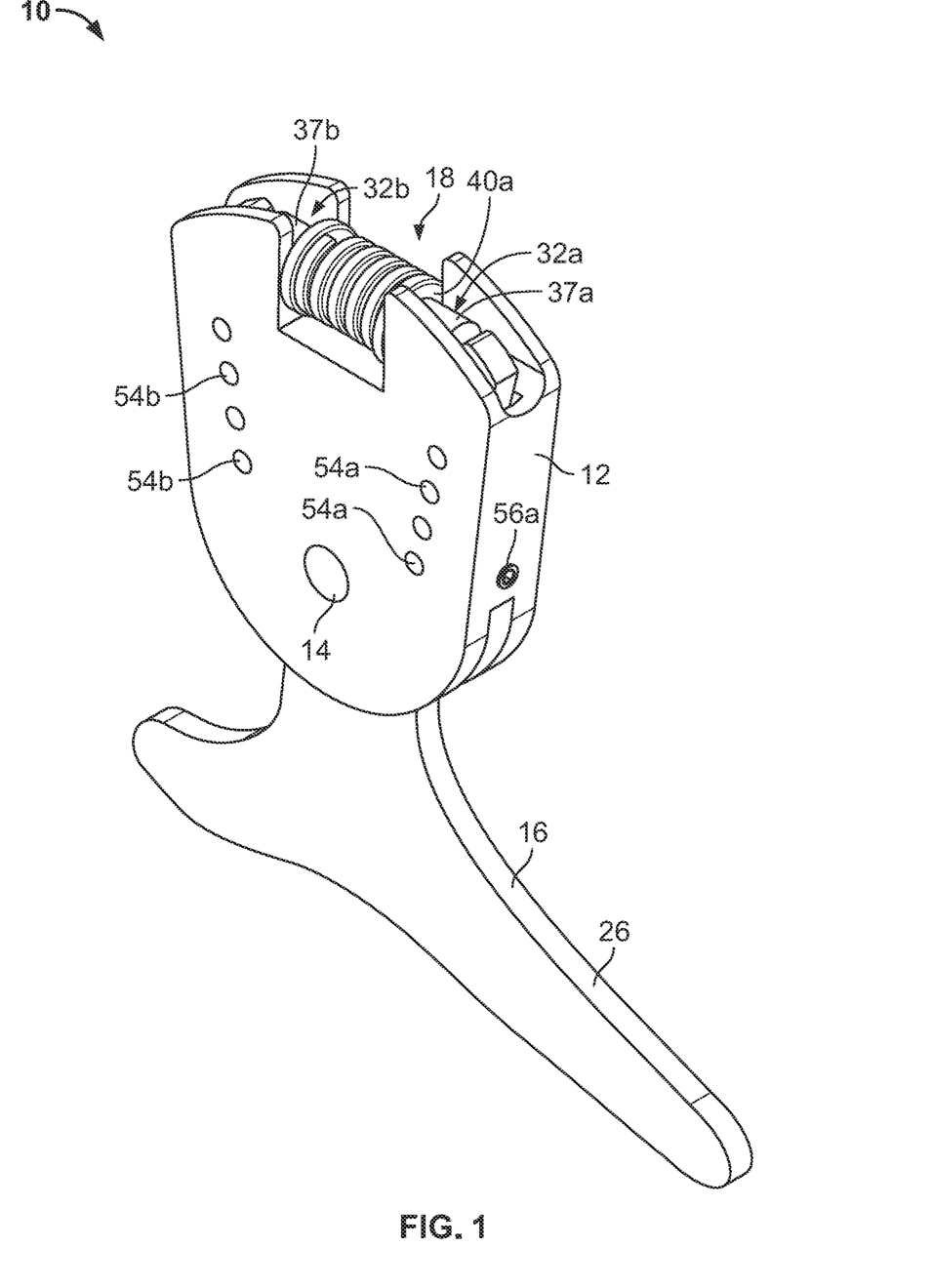
FIG. 1 is a perspective view of a joint for an ankle foot orthosis.
Figure 2:
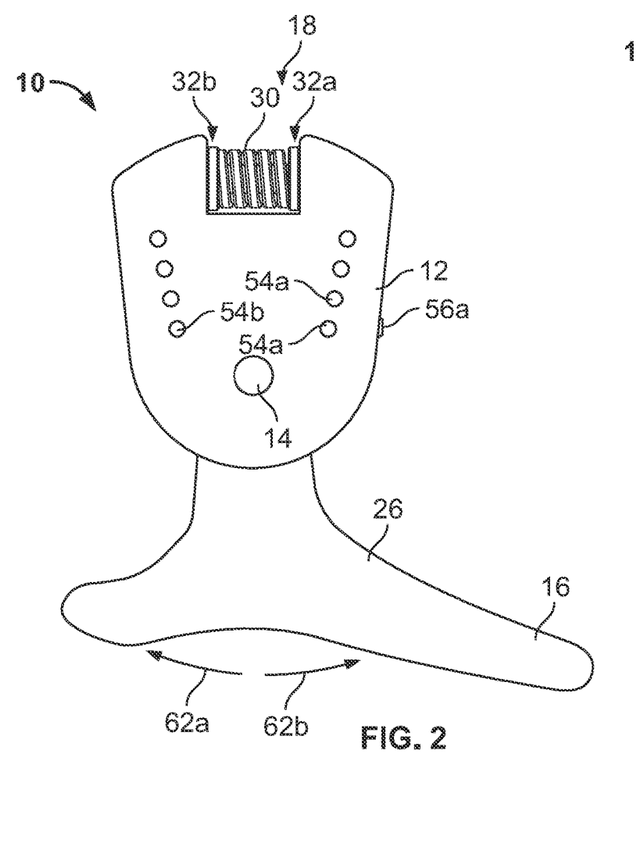
FIG. 2 is an elevation view of the joint of FIG. 1 from one side.
Figure 3:
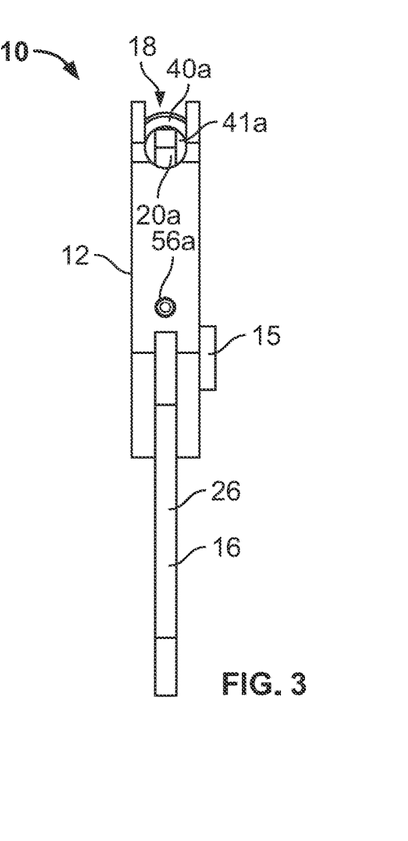
FIG. 3 is a front elevation view of the joint of FIG. 1.
Figure 4:
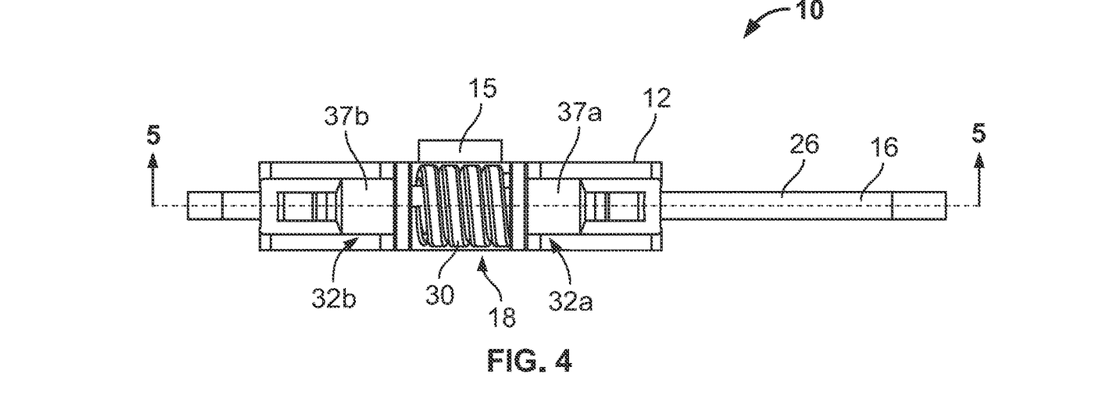
FIG. 4 is a plan view of the joint of FIG. 1.
Figure 5:
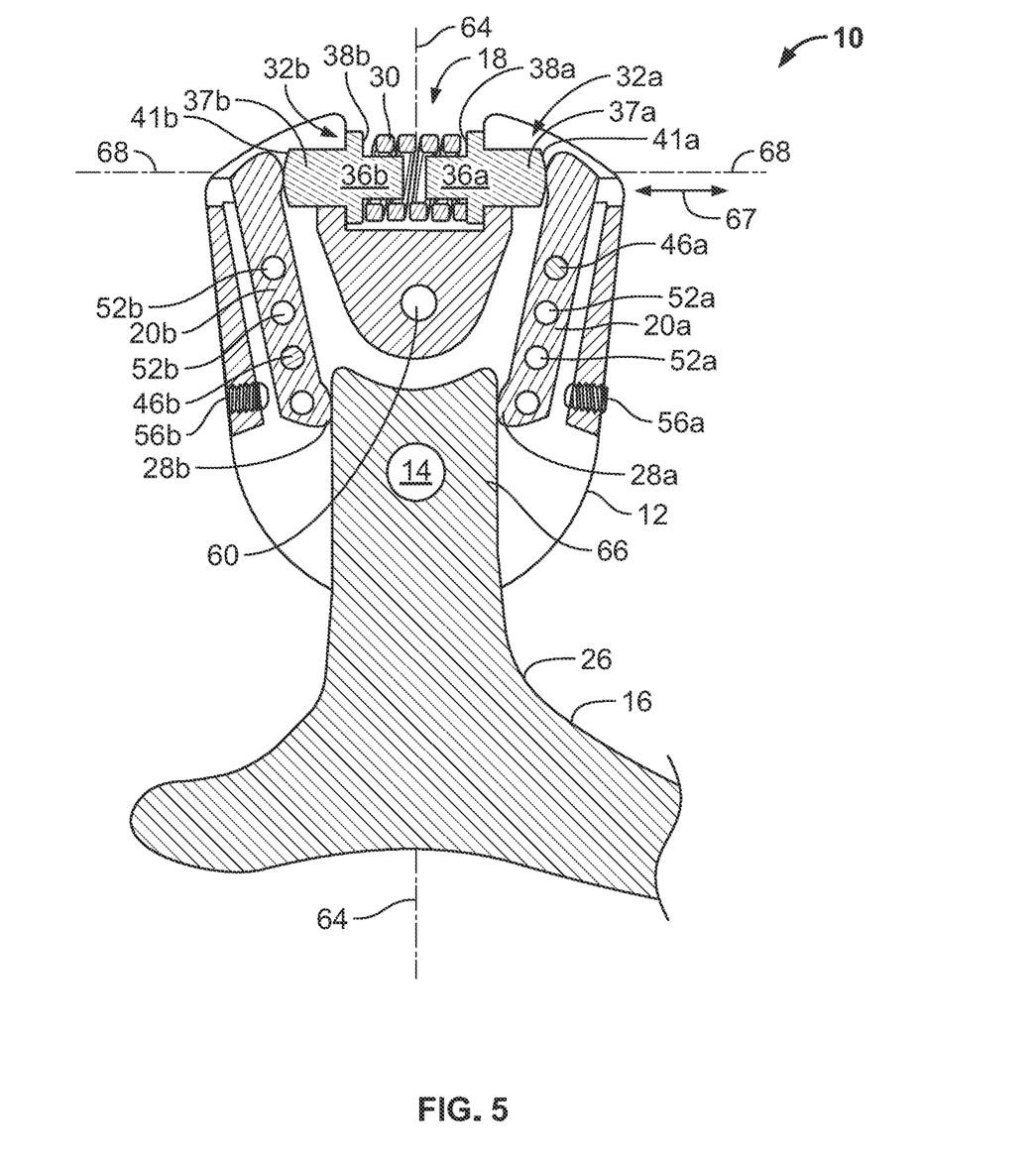
FIG. 5 is a cross-sectional view taken along line 5-5 shown in FIG. 4.
Figure 6:
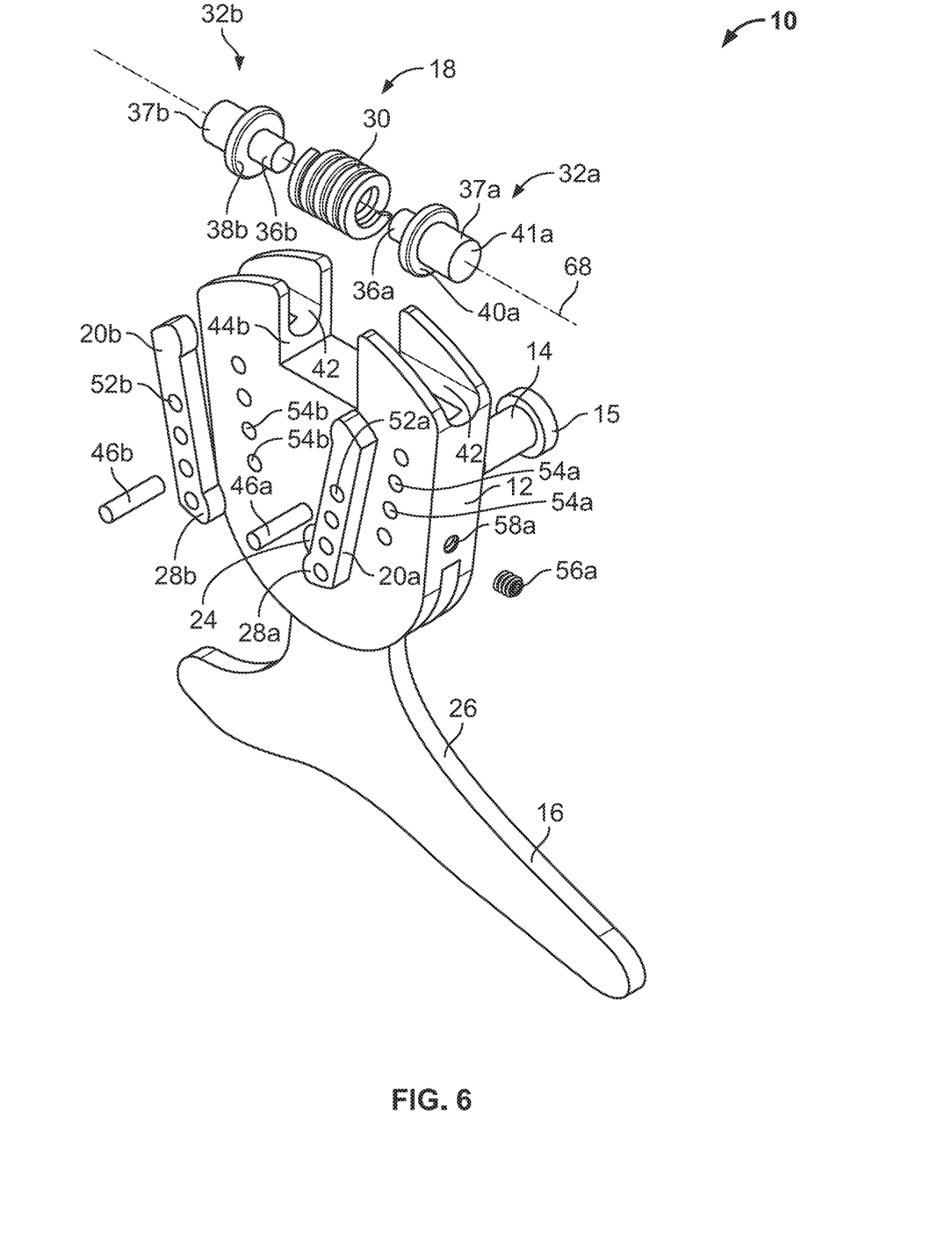
FIG. 6. is an exploded perspective view of the joint of FIG. 1

Attachment member 16 has a neutral position at which spring element 18 does not exert a net force on attachment member 16. Preferably, at the neutral position spring element 18 does exert a force in both the first and second directions, but the net force is zero, so that there is immediate resistance when the attachment member rotates away from the neutral position. Attachment member 16 has an axis 64 extending through the center of pivot 14 and the center of aperture 60. Axis 64 can be considered to be a central axis for an upper portion 66 of attachment member 16. In the neutral position, axis 64 corresponds to a neutral axis, which is substantially perpendicular to first and second followers' 30 direction of travel 67 and axis 68 of spring 30. As shown in FIG. 5, axis 64 and the neutral axis are vertical, and direction of travel 67 and axis 68 are horizontal. This perpendicular arrangement generally provides an optimal alignment for spring 30 for making joint device 10 compact.

A second embodiment of a joint device 110 is discussed with reference to FIGS. 11-16, which are schematic and show joint device 110 in a neutral position. Where parts are the same or similar to the first embodiment, reference numerals may be used which differ by 100 from the corresponding part in the first embodiment. Joint device 110 has a body 112 having a pivot 114, an attachment member 116, a spring element 118, a first lever 120a, and a second lever 120b. Pivot 114 is provided by pivot bushing 121, which fits within a pivot aperture 124 in joint body 112 and is held there by pivot screw 123. Attachment member 116 pivots around pivot 114 in first and second directions 162a and 162b. As shown, attachment member 116 is a stirrup 126 and joint device 110 is an ankle joint for use in an ankle-foot orthosis or a knee-ankle-foot orthosis. Stirrup 126 may be attached to a footplate (not shown) by any suitable means. Stirrup 126 has a crank portion 127 which contacts and is in between levers 120. Levers 120 are held in place against crank portion 127 by spring element 118, which is illustrated as a helical compression spring 130, but could be any suitable spring such as a machined spring or a combination of springs typically having very different characteristics, as discussed elsewhere.

Spring 130 holds first and second links, referred herein as first and second followers 132a and 132b, which push against first and second levers 120a and 120b. Each follower 132 has a cylindrical inner portion 136, an inside shoulder 138 and an end surface 141. Followers 32a and 32b may be identical as shown or may be different. Both inner portions 136 extend into spring 130. Spring 130 pushes against inside shoulders 138 pushing followers 132 outwardly. End surfaces 141 (a.k.a. follower surfaces 141) may be flat or curved. Some convexity to end surfaces 141 is generally preferred. Spring 130 pushes levers 120 against opposed internal sidewalls 143 in body 112 essentially seating levers 120 against internal sidewalls 143.

Returning back to levers 120, levers 120 rotate around pivots or fulcrums 146 provided by pins 148. The location of pins 148 are adjustable and may be held in place by any suitable means. For example, first and second sidewalls 143 may have a plurality of recesses (not shown) for holding pins 148 in a variety of positions. Alternatively, the fulcrum for the levers may be comprised of a slider nut, translated by an adjustment screw and pinned between the lever and an inner surface of the component body. Pin 148a is shown in a location which prevents the rotation of lever 120a (i.e., locking out lever 120a) and therefore prevents movement of stirrup 126 in the first direction.

Unlike joint device 10, joint device 110 also has a resist assembly 149, preferably two with one on either side of levers 20. As shown, each resist assembly 149 has a resist ball bearing 151, or alternatively a cylindrical pin with which to couple motion of the stirrup 30 to the springs 153a and 153b, a resist spring 153, a motion limiter pin 155, and a set screw 157. Each resist assembly 149 is located in a channel 159 in body 112. Set screw 157 is used to adjust the compression on spring 153 as well as determine the maximum active compression of the spring allowable until motion is limited by the motion limiter pin 155. Set screw 157 determines the preload force on stirrup 126 required to move away from its neutral position by adjusting the compression of the spring 153. Conceivably, resist spring 153 does not extend from resist ball bearing 151 to set screw 157 such that resist spring 153 does not initially resist rotation of stirrup 126, but instead provides resistance additional to spring 130/spring element 118 once stirrup 126 exceeds a specific rotation threshold. Resist spring 153 as shown is a coiled spring, but can be a helical spring or any suitable spring. Springs 153 push on ball bearings 151, but channels 159 are also designed to act as range of motion limiters to determine the maximum allowable excursion of the stirrup vis-a-vis the movement of the ball bearings 151 and compression of the springs 153.

Figures 14, 15:
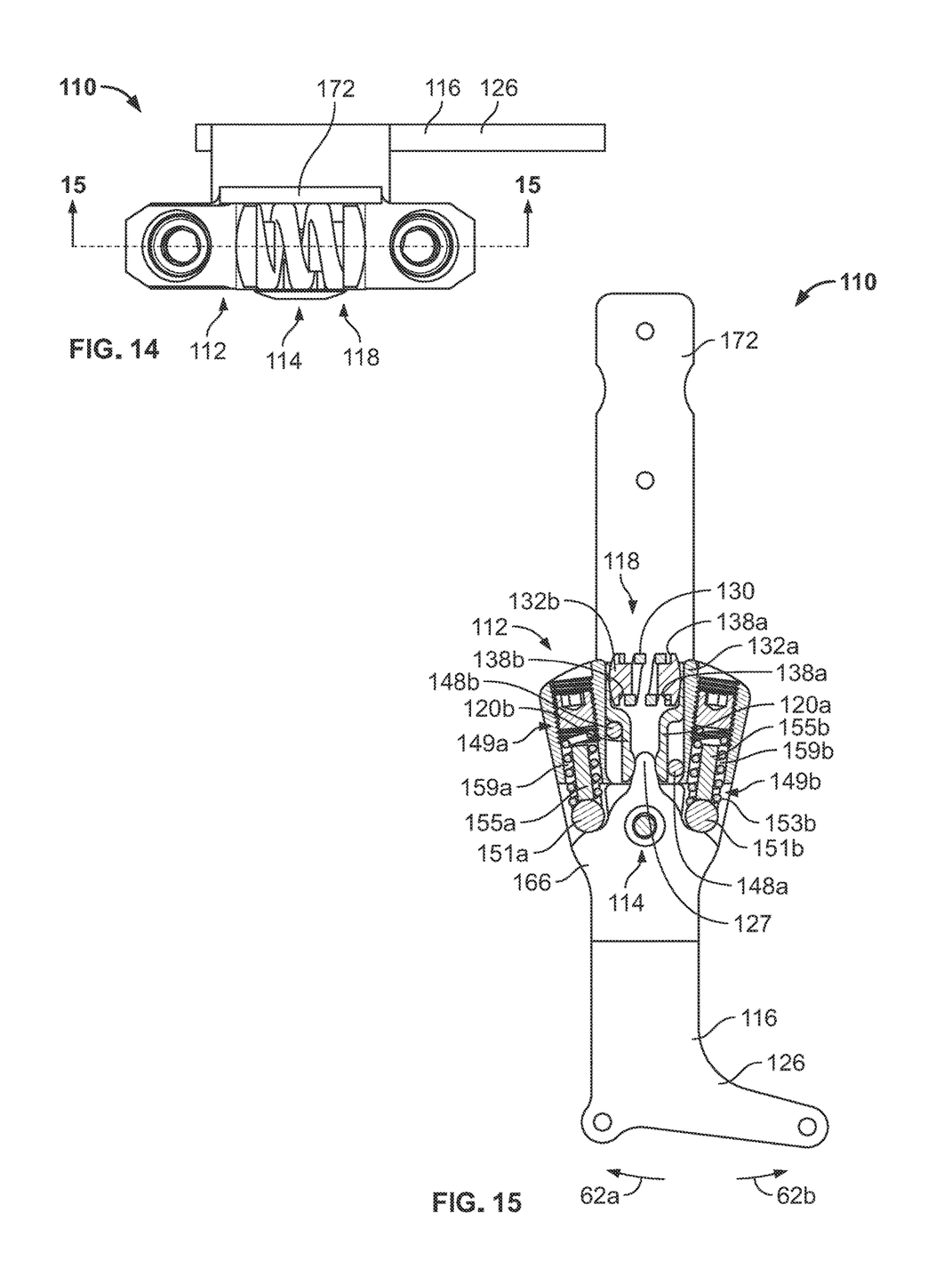
FIG. 14 is a plan view of the joint body of FIG. 11.
FIG. 15 is a cross-sectional view taken along line 15-15 shown in FIG. 14.
Figure 16:
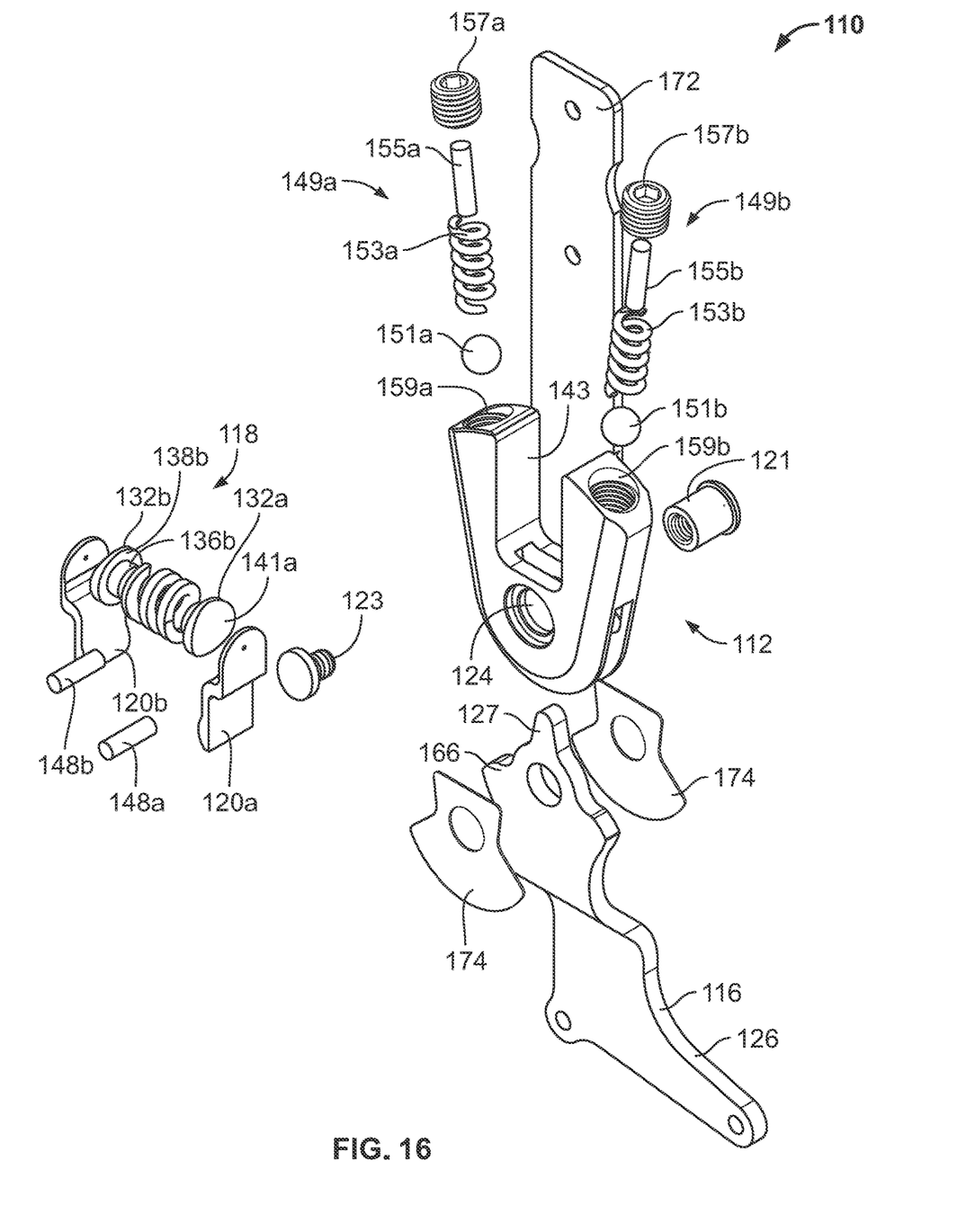
FIG. 16 is an exploded perspective view of the joint body of FIG. 11.

Attachment member 116 has a neutral position at which spring element 118 does not exert a net force on attachment member 116. Attachment member 116 has an axis 164 extending through the center of pivot 114. Axis 164 can be considered to be a central axis for an upper portion 166 of attachment member 16 including crank portion 127. Axis 164 can also be a central axis for second attachment member 172 particularly when it is fixed as shown here. In the neutral position, axis 164 is a neutral angle, which is substantially perpendicular to first and second followers' 132 direction of travel 167 and axis 168 of spring 130. As shown in FIG. 15, axis 164 and neutral angle are vertical, and direction of travel 167 and axis 168 are horizontal. This perpendicular arrangement generally provides an optimal alignment for spring 130 for making joint device 110 compact.

Joint device 110 also has a second, proximal attachment member 172. Joint device 110 may also include a pair of stirrup wear pads 174 to decrease off-axis and undesirable movements of the stirrup 126 while permitting smooth and unrestricted rotation of stirrup 126. Attachment member 172 is fixed as shown or can be movable relative to joint body 112. Attachment member 172 is in the form of a bar with two holes which can be attached to other orthotic components. Alternatively, attachment member 172 could be a rail box or other suitable structure for making joint device 110 part of an orthosis.

Operation of joint device 110 will now be discussed. FIGS. 11-16 illustrate joint device 110 in the neutral position in which attachment member 116 is at the neutral angle. As shown, attachment member 116 cannot be rotated in the direction 62a because pin 148a is in the way of crank portion 127 and lever 120a which may be desirable for some patients. This is the locked adjustment setting of pin 128a. If pin 148a was moved to a location upward of crank portion 127, it would be possible to rotate attachment member 116 in direction 62a. It is not necessary to discuss this possible rotation because of its similarity to the rotation in direction 62b, which is discussed next. When attachment member 116 is rotated in direction 62b, crank portion 127 pushes against lever 120b which rotates around pin 148b thereby pushing follower 132b and compressing spring 130/spring element 118. At the same time, attachment member 116 pushes resist ball bearing 151b upwardly thereby compressing resist spring 153b against set screw 157b. Further rotation in direction 62b is possible until followers 132 contact each other or resist ball bearing 151b pushes limiter pin 155b against set screw 157b. During this rotation, resist ball bearing 151a is seated at the bottom of channel 159 by resist spring 153a, which acts to limit the excursion of ball bearing 151a such that it cannot follow the stirrup 116 as the stirrup moves away from ball bearing 151a. Lever 120a remains more or less in the same position as it is held in place by spring 130 and follower 132a against sidewall 143a.

A push-pull joint device (not illustrated) is also possible. Such a device could take many forms including one similar to ankle joint device 10. Instead of two levers 20, it would have a single one. Lever 20 would be connected by one rigid link to stirrup 26 and by another rigid link to spring 30 so that push and pull forces could be transmitted to and from stirrup 26 from and to spring 30. Spring 30 would not just be subject to compression, but also to tension.

Orthosis

In a preferred embodiment of an orthosis (not shown), which can be an ankle foot orthosis (AFO) or a knee ankle foot orthosis (KAFO), the orthosis includes one or more joint devices, such as joint devices 10 and 110. Two joint devices may be used on opposite sides of the same joint, for example. The orthosis has first and second attachment members, one of which is configured for attachment to a lower leg of a human wearer of the device, and the other being configured for attachment to a foot of a human wearer of the device. One of the attachment members can correspond to attachment members 16 and 116, and may be attached to a footplate (not shown) by any suitable means, e.g. by being laminated into the structure of the footplate, attached using mechanical fasteners or encapsulated by manual vacuum thermoforming a polymer sheet around the stirrup. The other attachment member can correspond to attachment member 172 or to an attachment member connected to a joint device 10 by aperture 60. The other attachment member is connected to the lower leg of a wearer by any suitable means including bracing, straps, pads, etc. In an AFO or KAFO, first direction 62a is a plantarflexion direction and the second direction 62b is a dorsiflexion direction.

Method of Use

A method of supporting an ankle of a human in a range of dorsiflexion and plantarflexion motions is also provided for the orthosis previously discussed. The first attachment member is attached to a lower leg or foot corresponding to said ankle. The second attachment member is attached to the other lower leg or foot. The joint device, whether device 10, device 110 or another, can have a plantarflexion range of motion up to about 20° (π/9 rad) and a dorsiflexion range of motion up to about 20° (π/9 rad). An orthotist can limit these ranges to match the needs of the wearer.

While the invention has been described with respect to certain embodiments, as will be appreciated by those skilled in the art, it is to be understood that the invention is capable of numerous changes, modifications and rearrangements, and such changes, modifications and rearrangements are intended to be covered by the following claims.

What is claimed is:

1. An orthotic joint device comprising:
  an attachment member rotatably attached to the joint device for rotation about a joint pivot of the joint device in a first direction and in a second direction opposed to the first direction;
  a resistive element for resisting rotation of the attachment member in the first direction; and
  a first lever for transmitting a first direction resistance force from the resistive element to the attachment member, the first lever having a first pivot that is not concentric with the joint pivot;
  wherein the resistive element resists the rotation of the attachment member in the first direction when the attachment member's rotation in the first direction exceeds a first direction rotation threshold.

2. The device of claim 1 further comprising a first mechanical advantage of the resistive element acting on the attachment member by the first lever, the location of the first pivot being selectable to select the first mechanical advantage.

3. The device of claim 2 further comprising a plurality of first lever apertures, a first lever pivot pin, wherein the location of the first pivot is selectable by placing the first lever pivot pin in one of the first lever apertures.

4. The device of claim 3 wherein the plurality of first lever apertures comprises an aperture in which placement of the first lever pivot pin prevents rotation of the attachment member in the first direction.

5. The device of claim 2 wherein the first lever comprises the first lever apertures.

6. The device of claim 1 further comprising a first link, wherein the first lever presses against the first link and the first link presses against the resistive element when rotation of the attachment member in the first direction exceeds the first direction rotation threshold.

7. The device of claim 6 wherein the first link comprises a first follower having a first follower shoulder, the device further comprising a first follower seat, wherein the first follower shoulder is engaged with the first follower seat when rotation of the attachment member in the first direction is less than the first direction rotation threshold and is not engaged with the first follower seat when rotation of the attachment member in the first direction exceeds the first direction rotation threshold.

8. The device of claim 7 wherein the first follower has a first follower surface against which the first lever presses when the attachment member's rotation in the first direction exceeds the first direction threshold, wherein the first lever has a neutral angle position when the attachment member is in a neutral position and the first lever is in contact with the attachment member, the first direction threshold being a function of a distance between the first follower surface and the first lever in the neutral angle position.

9. The device of claim 7 wherein the resistive element comprises a spring element, the device further comprising a neutral axis, the neutral axis being the central axis for at least an upper portion of the attachment member when the attachment member is at rest and is in a position at which the resistive element does not exert a net force on the attachment member, wherein the first follower has a direction of travel that is substantially perpendicular to the neutral axis.

10. The device of claim 1 wherein the resistive element comprises a spring element, the device further comprising a neutral axis, the neutral axis being the central axis for at least an upper portion of the attachment member when the attachment member is at rest and in a position at which the resistive element does not exert a net force on the attachment member, wherein the spring element comprises a spring from the group consisting of a coil spring, a machined helical spring, cup springs, and combinations thereof, the spring element having an axis of compression that is substantially perpendicular to the neutral axis.

11. The device of claim 1 further comprising a first adjustable range of motion limiter for limiting the range of motion in the first direction.

12. The device of claim 11 wherein the device further comprises a first threaded passage, the first adjustable range of motion limiter comprising a first threaded screw whose location in the first passage is adjustable by screwing the first threaded screw in or out.

13. The device of claim 1 further comprising a first adjustable preload spring for adjusting the preload force resisting the rotation of the attachment member in the first direction.

14. The device of claim 1 further comprising a second lever for transmitting a second direction resistance force from the resistive element to the attachment member, wherein the resistive element also resists the rotation of the attachment member in the second direction when the attachment member's rotation in the second direction exceeds a second direction rotation threshold.

15. The device of claim 14 further comprising a first follower, wherein the resistive element comprises a spring element, wherein the first lever presses against the first follower and the first follower presses against the spring element when rotation of the attachment member in the first direction exceeds the first direction rotation threshold, and
  a second follower, wherein the second lever presses against the second follower and the second follower presses against the spring element when rotation of the attachment member in the second direction exceeds the second direction rotation threshold.

16. The device of claim 15 wherein the first follower has a first follower shoulder, the device further comprising a first follower seat, wherein the first follower shoulder is engaged with the first follower seat when rotation of the attachment member in the first direction is less than the first direction rotation threshold and is not engaged with the first follower seat when rotation of the attachment member in the first direction exceeds the first direction rotation threshold; and wherein the second follower has a second follower shoulder, the device further comprising a second follower seat, wherein the second follower shoulder is engaged with the second follower seat when rotation of the attachment member in the second direction is less than the second direction rotation threshold and is not engaged with the second follower seat when rotation of the attachment member in the second direction exceeds the second direction rotation threshold.

17. The device of claim 1 wherein the first lever is connected to the resistive element in a push-pull arrangement.

18. An orthosis for a human, the orthosis comprising:
  an orthotic joint device comprising (1) a first attachment member rotatably attached to the joint device for rotation about a joint pivot of the joint device in a first direction and in a second direction opposed to the first direction, (2) a resistive element for resisting rotation of the attachment member in the first direction, (3) a first lever for transmitting a first direction resistance force from the resistive element to the first attachment member, the first lever having a first pivot that is not concentric with the loint pivot, wherein the resistive element resists the rotation of the first attachment member in the first direction when the attachment member's rotation in the first direction exceeds a first direction rotation threshold, and (4) a second attachment member attached to the orthotic joint device;
  one of the first attachment member and the second attachment member being configured for attachment to a lower leg of the human, and the other being configured for attachment to a foot of the human.

19. The orthosis of claim 18 further comprising a joint body wherein the second attachment member is configured for attachment to the lower leg and may be rotated and locked relative to the joint body.

20. A method of supporting an ankle of a human in a range of dorsiflexion and plantarflexion motions, using an ankle foot orthosis comprising an orthotic joint device comprising (1) a first attachment member rotatably attached to the joint device for rotation in a plantarflexion direction and in a dorsiflexion direction opposed to the plantarflexion direction about a joint pivot of the joint device, (2) a resistive element for resisting rotation of the first attachment member in the plantarflexion direction, (3) a first lever for transmitting a plantarflexion direction resistance force from the resistive element to the first attachment member, the first lever having a first pivot that is not concentric with the joint pivot, wherein the resistive element resists the rotation of the first attachment member in the plantarflexion direction when the first attachment member's rotation in the plantarflexion direction exceeds a plantarflexion direction rotation threshold, and (4) a second attachment member attached to the orthotic joint device, the method comprising:

attaching the first attachment member to a lower leg or foot corresponding to said ankle; and     attaching the second attachment member to the other of the foot and the lower leg.

\* \* \* \* \*

UNITED STATES PATENT AND TRADEMARK OFFICE
CERTIFICATE OF CORRECTION

PATENT NO. : 11,911,306 B2
APPLICATION NO. : 17/784534
DATED : February 27, 2024
INVENTOR(S) : Nicholas Lecursi and Beatrice Janka It is certified that error appears in the above-identified patent and that said Letters Patent is hereby corrected as shown below:

In the Specification

Column 5, Line 28, delete "FIG. 1" and insert -- FIG. 1. --.

Column 8, Lines 18-19, replace "162a and 162b" with -- 62a and 62b --.

In the Claims

Column 11, Claim 5, Line 12, replace "claim 2" with -- claim 3 --.

Signed and Sealed this
Twenty-third Day of April, 2024

Katherine Kelly Vidal
*Director of the United States Patent and Trademark Office*